(12) United States Patent
Cranton et al.

(10) Patent No.: US 9,110,034 B1
(45) Date of Patent: Aug. 18, 2015

(54) NIGHT VISION DEVICE TEST APPARATUS

(71) Applicant: L-3 Communications Corporation, Warrior Systems Division, Londonderry, NH (US)

(72) Inventors: Brian W. Cranton, Sanbornton, NH (US); Peter D. Braudis, Groton, MA (US); Mark A. Blais, Weare, NH (US)

(73) Assignee: L-3 Communications Corp., Londonderry, NH (US)

( * ) Notice: Subject to any disclaimer, the term of this patent is extended or adjusted under 35 U.S.C. 154(b) by 0 days.

(21) Appl. No.: 14/485,929

(22) Filed: Sep. 15, 2014

Related U.S. Application Data

(60) Provisional application No. 61/878,324, filed on Sep. 16, 2013.

(51) Int. Cl.
*G01D 18/00* (2006.01)
*G01N 21/88* (2006.01)

(52) U.S. Cl.
CPC .... *G01N 21/8806* (2013.01); *G01N 2021/8841* (2013.01)

(58) Field of Classification Search
CPC .......................... G01T 1/1645; H01J 2231/50
See application file for complete search history.

(56) References Cited

U.S. PATENT DOCUMENTS

2008/0054166 A1* 3/2008 Kuzniz et al. ........... 250/214 VT

* cited by examiner

*Primary Examiner* — Kiho Kim

(57) ABSTRACT

Night vision devices utilize image intensifier tubes to see in low light conditions. A man-portable tester allows an operator to check for defects and determine the image resolution of the image intensifier tube quickly and easily without a power source or a darkened room.

20 Claims, 10 Drawing Sheets

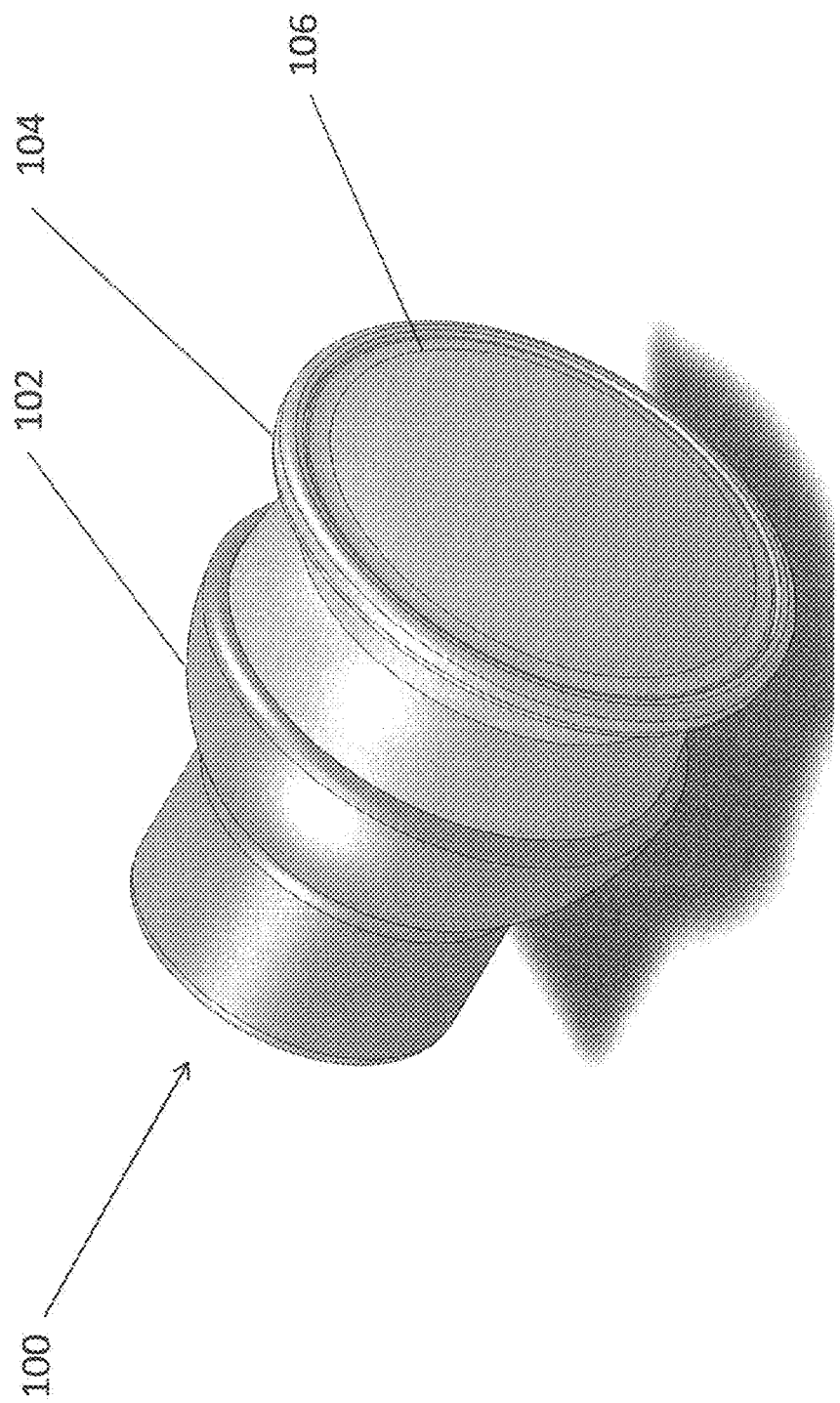

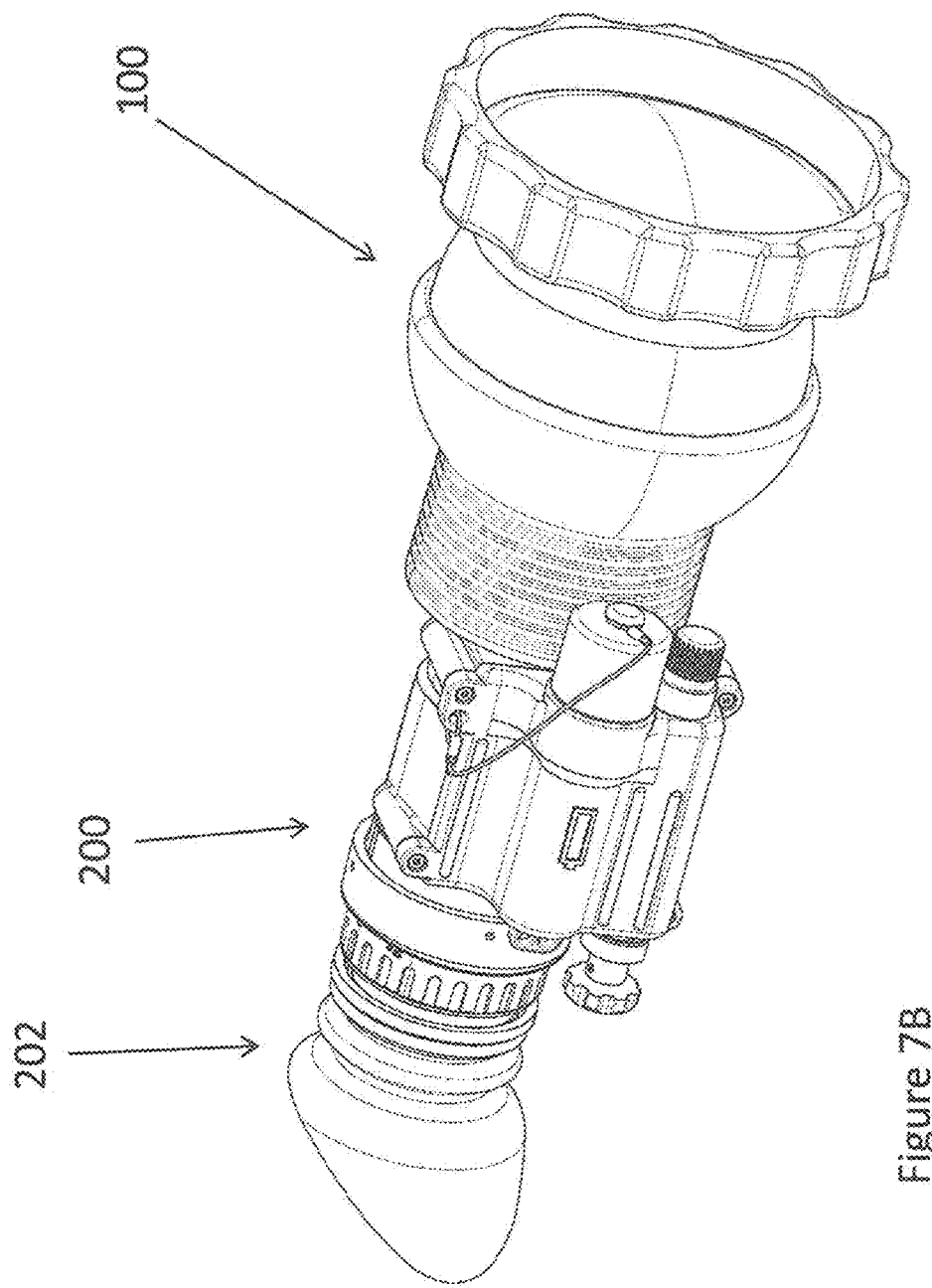

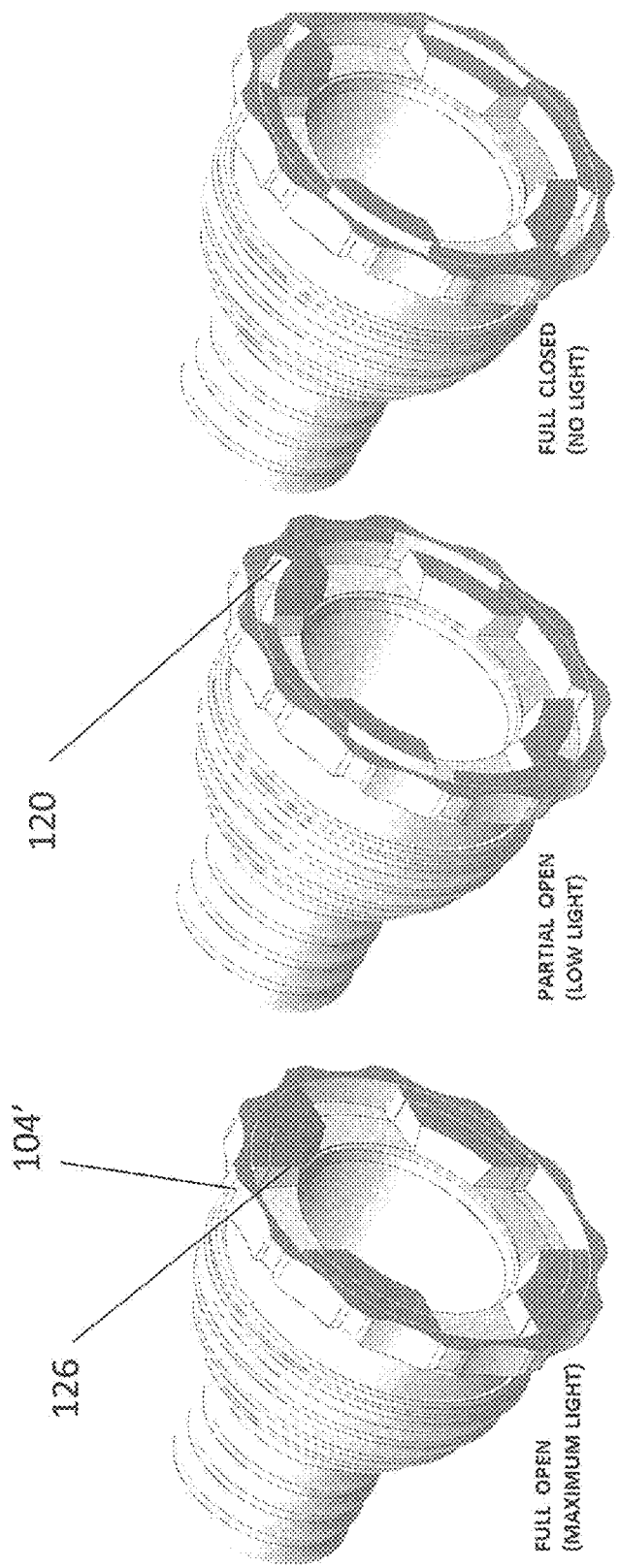

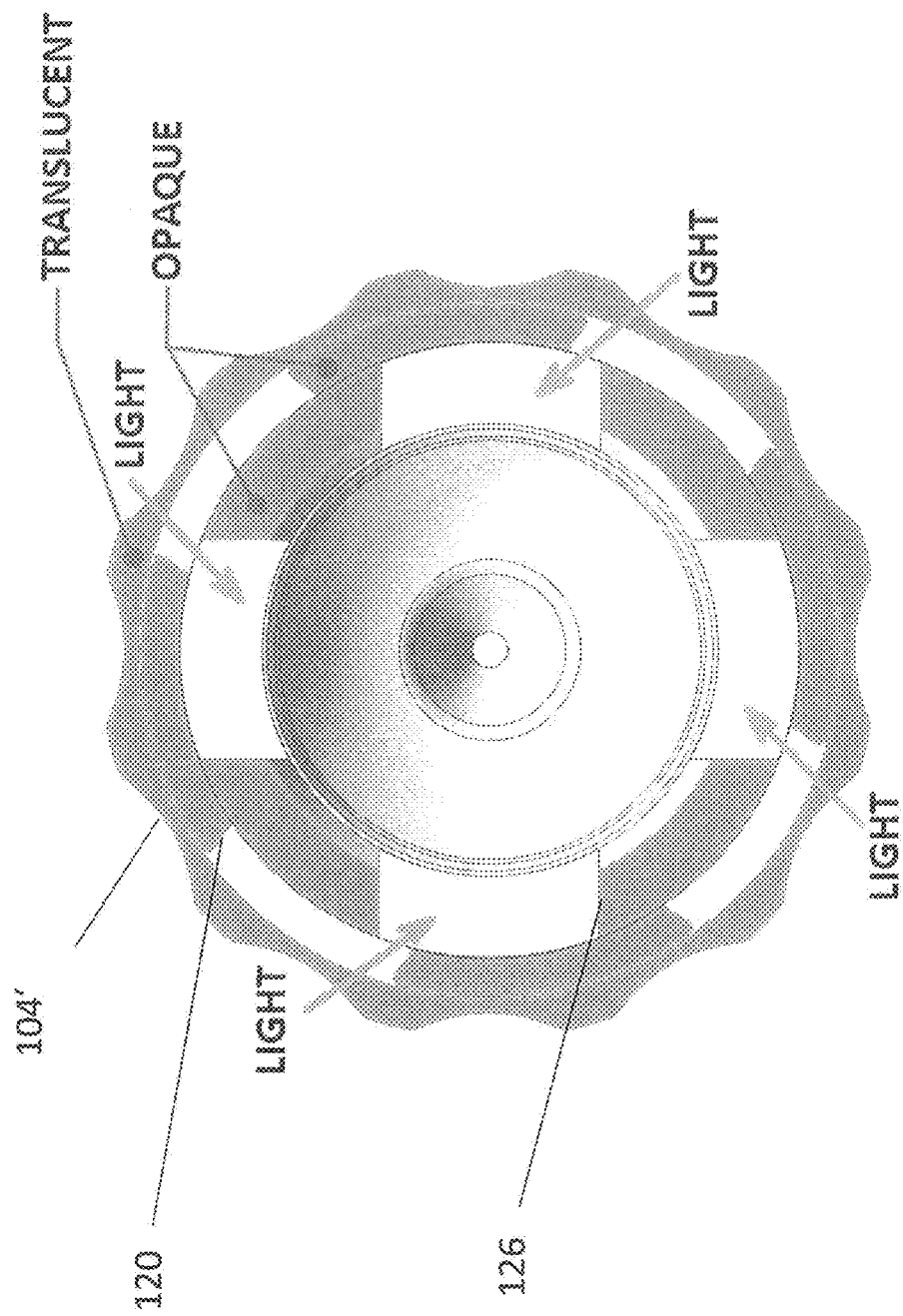

NIGHT VISION DEVICE TEST APPARATUS

CROSS REFERENCE TO RELATED APPLICATIONS

This application claims the benefit of U.S. Provisional patent application Ser. No. 61/878,324 filed Sep. 16, 2013, the entire disclosure of which is incorporated herein by reference in its entirety.

TECHNICAL FIELD

The present disclosure relates to test apparatus for night vision system with image intensifier tubes.

BACKGROUND

Soldier and law enforcement personnel use night vision devices, e.g. the AN/PVS-14, that include an image intensifier tube to allow them to see under very low light conditions. Before these devices are sent out on a mission they need to be tested to ensure they work properly. The most widely used image intensifier test set is the TS-4348/UV "Test Set, Electronic Systems" (a.k.a "Assessor") and has been in production since approximately 1992 (see FIG. 1). The TS-4348/UV is compact and lightweight. The functionality of the TS-4348/UV is controlled by MIL-PRF-49318A which states "The Assessor is a self-contained, battery operated, test device designed to provide a Go/No-Go check of the night vision systems . . . . " The Go/No-Go check is accomplished by projecting a USAF 1951 bar target (a sample is shown in FIG. 2) into a night vision system, at controlled light levels, in a manner that allows the resolution of the night vision system to be measured near the optical axis. The TS-4348/UV uniformly illuminates the field of view of the night vision system under test and illumination intensity is electronically controlled with precise opto-electronic feedback. The TS-4348/UV does not provide a means to identify defect (black spot and white spots) location or size, or for performing off-axis resolution tests.

The most common current method of identifying and measuring defects is with the use of a paper chart approximately 22.5"×30" in size (see FIG. 3) mounted on a wall. The test involves holding a night vision device 30"±1" from the chart, viewing perpendicular to the chart, and centered on the concentric circles in a room whose light level can be adjusted from bright to dark. Black spots are identified with the room lights on, white spots are identified with the room completely dark, and other defects when the light level is low. Once defects are identified, the concentric rings are used to identify the zone in which the defect falls. The device is then repositioned to place the defect next to the black circles on the target which allow for defect size measurement. The number of defects and zones in which they fall are compared to a specification to determine the acceptability of the tube in a Go/No-Go style test. The wall chart does not provide a resolution test and requires a room with controllable lighting.

The Hoffman ANV-126A (see FIG. 4) is a high end night vision tester with significantly more functionality than the TS-4348/UV or a wall chart. The ANV-126A performs resolution testing with a USAF 1951 bar target similar to the TS-4348/UV but with much greater electronic control over illumination levels and can perform defect zone mapping similar to a wall chart. A number of additional tests, such as measuring tube gain and tube current draw can also be performed which the TS-4348/UV, wall chart cannot perform. The drawbacks are in cost, complexity, and portability; an ANV-126A retails for approximately $40,000 while an Assessor is approximately $1000 and a wall chart less than $100. The weight of an ANV-126A exceeds 20 pounds while both the TS-4348/UV and wall charts are less than 1 pound each. The TS-4348/UV requires batteries to operate and the ANV-126A requires access to AC power. The TS-4348/UV and wall charts are commonly used in Army repair enclosures, such as the AN/ASM-146 or AN/ASM-147, while the ANV-126A is considered unsuitable for those environments.

The modern image intensifier tube dates back to the 1970's and was used in military devices such as the AN/PVS-4 night vision weapon sight and AN/PVS-5 night vision goggle. These early devices used what was referred to as $2^{nd}$ generation image intensification tubes. Current state of the art night vision devices use $3^{rd}$ generation image intensification tubes which function on the same principles as the $2^{nd}$ generation tubes with some evolutionary improvements. Test equipment to evaluate and diagnose night vision devices with image intensification tubes has been developed over the years. Testers include the 1990's vintage TS-4348/UV low light resolution tester, wall charts, or the Hoffman Engineering ANV-126-001 night vision goggle tester, noted above.

Field test equipment is desirable to support logistics. Shipping damage, degradation during shipping, or failed vendor quality checks can lead to a new image intensifier tube being unsuitable prior to use. Good image intensification tubes are expensive and have a limited life span over which their performance will slowly degrade, and it is desirable to identify the point at which a tube has degraded to the point where replacement is merited. Finally, night vision systems are typically used in potentially hostile environments such as by the military, search and rescue, and police, which can result in a night vision system being damaged. When damage occurs, convenient methods and tools to diagnose the damage are needed in order to determine if repairs are needed.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIG. 5 is a computer rendering of a night vision testing device consistent with a first embodiment of the present disclosure;

FIG. 7B is a isometric view of a night vision device inserted into an end of the night vision testing device of FIG. 5;

FIG. 10A is an isometric section view of the night vision testing device of FIG. 9 in a first position, FIG. 10B is an isometric section view of the night vision testing device of FIG. 9 in a second position, and FIG. 10C is an isometric section view of the night vision testing device of FIG. 9 in a third position; and FIG. 11 is an section view of the night vision testing device of FIG. 9.

DETAILED DESCRIPTION

Figure 2:
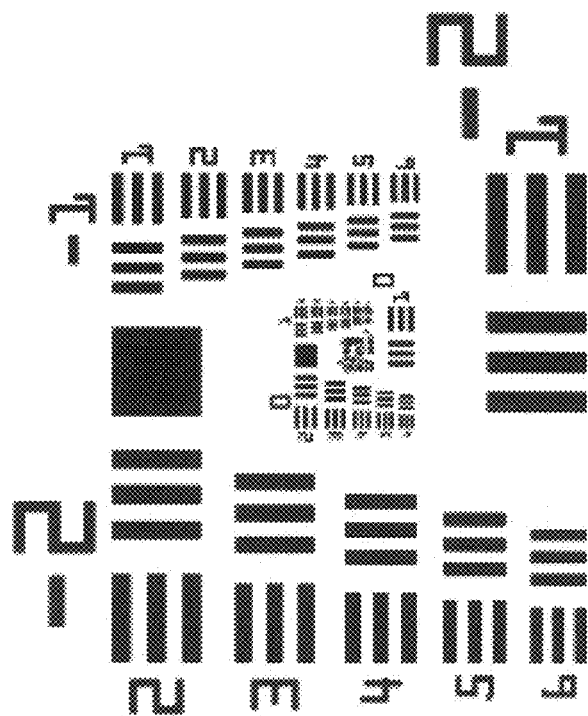
FIG. 2 is a sample 1951 United States Air Force resolution chart.
Figure 1:
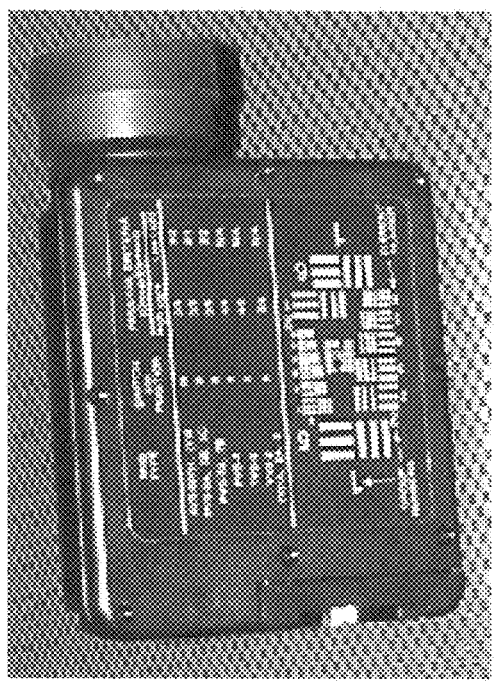
FIG. 1 is a photo of a TS-4348/UV Test Set, Electronic System.
Figure 4:
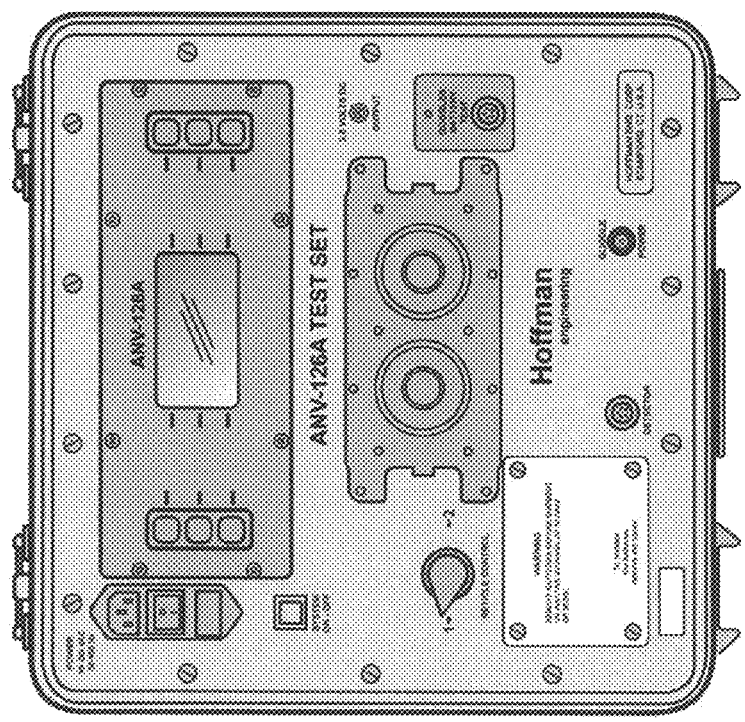
FIG. 4 is photo of a Hoffman ANV-126A.
Figure 3:
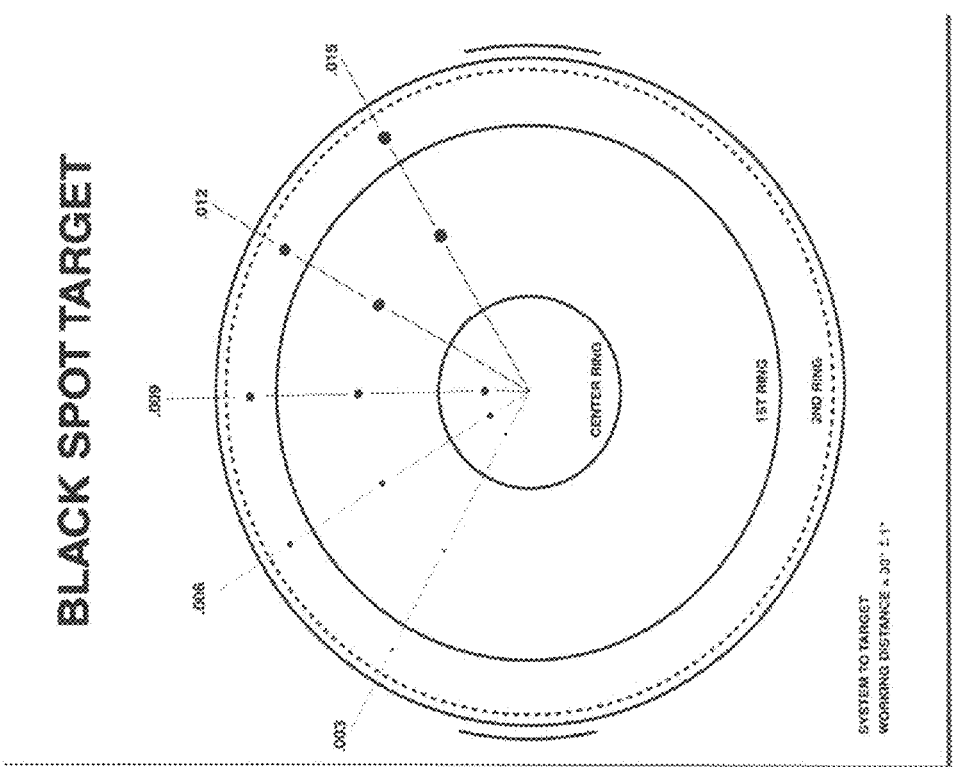
FIG. 3 is a "Black Spot Target" wall chart.
Figure 6:
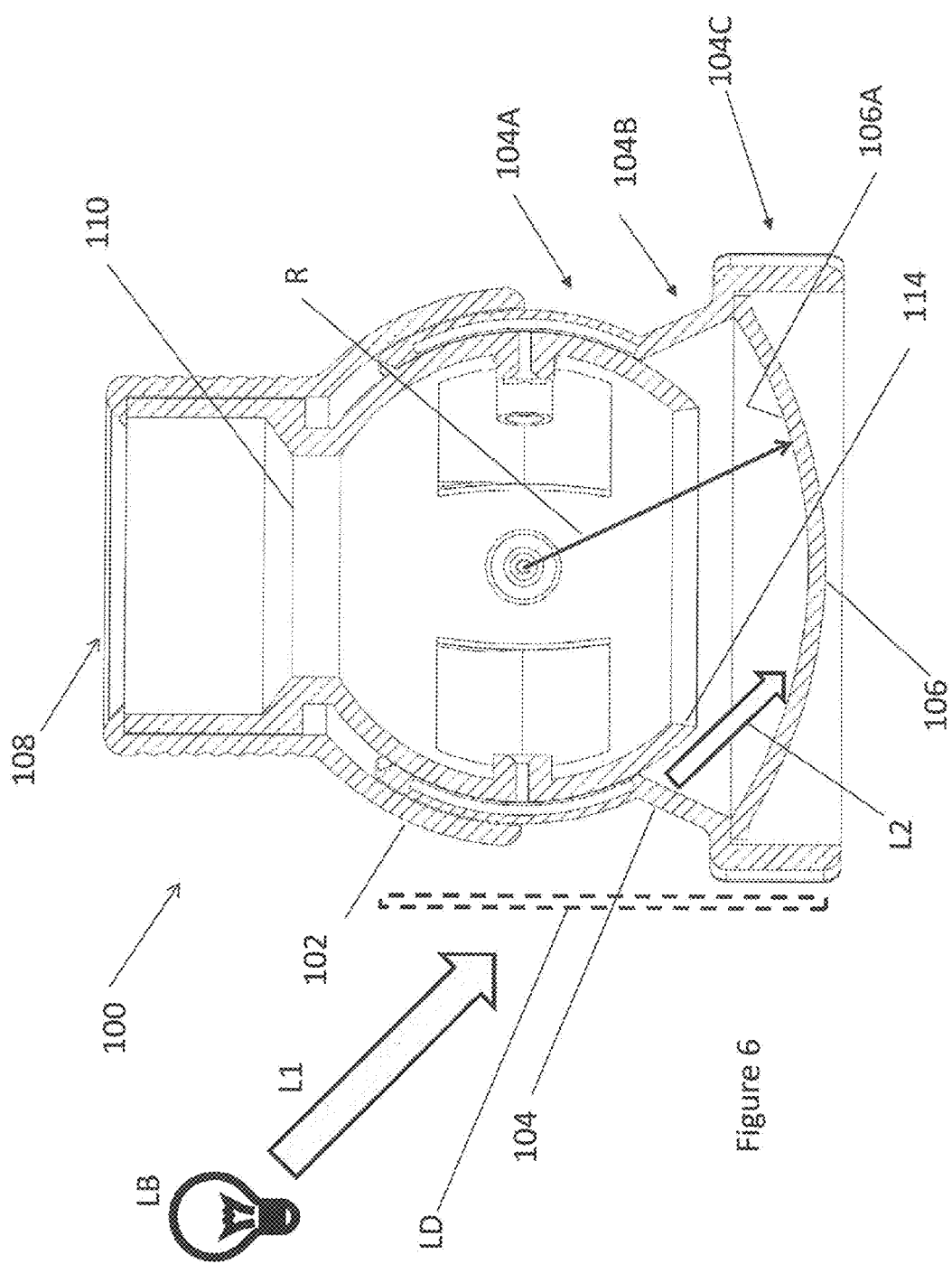
FIG. 6 is a section view of the night vision testing device of FIG. 5.
Figure 7A:
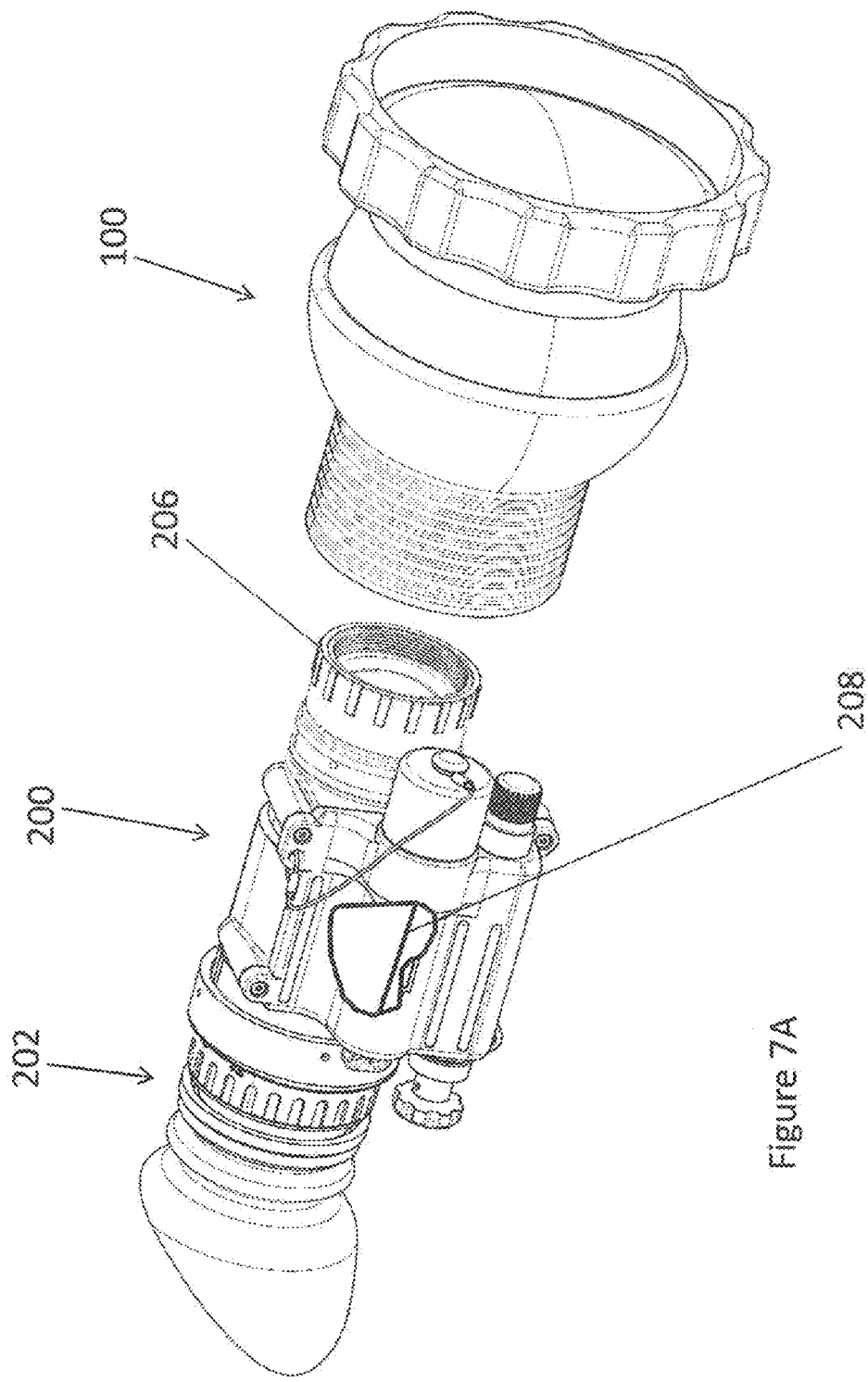
FIG. 7A is a isometric view of a night vision device spaced from the night vision testing device of FIG. 5

FIG. 5 is a computer rendering of a night vision testing device 100 consistent with a first embodiment of the present disclosure; FIG. 6 is a section view of the night vision testing device 100; FIG. 7A is a isometric view of a night vision device 200, shown as a monocular, spaced from the night vision testing device 100; and FIG. 7B is a isometric view of the night vision device 200 inserted into an end of the night vision testing device 100. The testing device 100 allows identification of image intensifier tube 208 defects and determination of resolution operating in darkness, bright conditions, and high contrast lighting conditions. Identification involves determining the zone in which defect appears, the size of defect, and type of defect. The four most common defect types are dark spots, bright spots, scintillation, and chicken wire.

Figure 8:
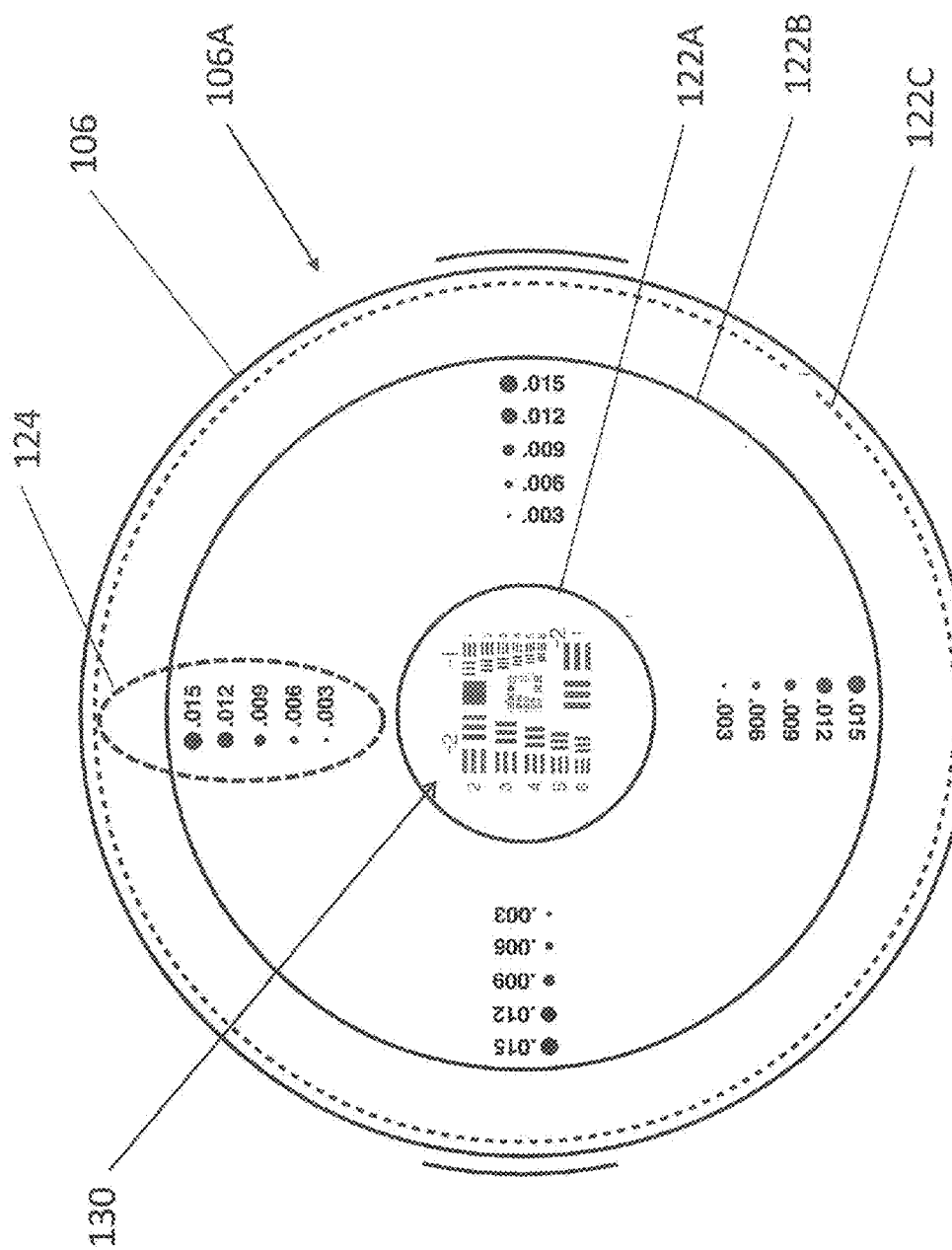
FIG. 8 is a first embodiment of a target inside of the night vision testing device of FIG. 5.

The testing device 100 may have a first portion 102 and a second portion 104 that pivots relative to the first portion 102, for example, they may work like a ball-and-socket joint. The pivot allows the night vision device 200 to be rotated relative to a target 106A in order to place target features in different areas of the night vision device field of view. In order to maintain a well focused image across the field without requiring mechanical adjustment of the night vision device this pivot is preferably placed close to the center of curvature of the spherically shaped target. On the second portion 104 may be a cover 106 which may house the target 106A (see FIG. 8). Optics 110 may include a optics and/or neutral density filter inserted in an opening 108 of the testing device 100. The optics and/or neutral density filter may be located close to the entrance aperture of the night vision device 100 and may act to reimage the target 106A onto the image intensifier tube of the night vision device. The distance at which the target appears to be from the night vision system under test may be configurable through optics 110. Two typical apparent target distances are 30" to mimic the standard dark spot wall chart test and infinity which is the commonly used as a zero diopter setting for test targets. The stop size of optics 110 may be chosen to balance aberrations, diffraction, and light throughput. The neutral density filter may have an optical density of 0 to about 3.

The opening 108 may be sized to accept an objective focus ring 206 of the night vision device 200. The size of the opening 108 may be such that when the focus ring 206 is inserted into the opening 108, a user can hold the night vision device 200 in one hand and the first portion 102 of the testing device 100 with the other hand, and when the night vision device 200 is rotated, the focus ring 206 is rotated relative to the night vision device 200. The user can turn "on" the night vision device 200, look through the eyepiece 202 and rotate the night vision device 200 relative to the first portion 102 to bring the target 106A into focus. In an alternative embodiment, an insert may be inserted in the opening to change the diameter of the opening to accommodate objective focus rings of differing sizes. In an alternative embodiment, the interface at opening 108 may be an interchangeable component to accommodate different night vision devices. In an alternative embodiment, the user can hold the second portion 104 of the testing device 100 rather than the first portion 102.

The second portion 104 of the testing device 100 may have a curved portion 104A that cooperates with the first portion 102; a middle portion 104B; and a base portion 104C that may hold the cover 106. The cover 106 may have a curved internal surface having a radius R upon which the target 106A is disposed. The target 106A may have a center ring 122A sized that when viewed through the night vision device 200 corresponds to "Zone 1" of an image intensifier tube. Zone 1 may be sized to appear as a 0.22 inch diameter ring on the entrance of the image intensifier tube in the night vision device 200. The target 106A may have a second ring 122B sized that when viewed through the night vision device 200 corresponds to "Zone 2" of an image intensifier tube. Zone 2 may be sized to appear as a 0.58 inch diameter ring on the entrance of the image intensifier tube in the night vision device 200. The target 106A may have a third ring 122C sized that when viewed through the night vision device 200 corresponds to "Zone 3" of an image intensifier tube. Zone 3 may be sized to appear as a 0.71" inch diameter ring on the entrance of the image intensifier tube in the night vision device 200. The diameters of the zone may be changed without departing from the invention to match the requirements of different image intensifier tube specifications (e.g. "MIL-PRF-A3256363D (CR)"). The target 106A may also have a series of measurement features 124, for example circles of different sizes. The series of circles, when imaged through night vision device 200, may range from approximately 0.003" in diameter to approximately 0.015" in diameter on the entrance of the image intensifier tube. The circles may be solid/filled in or hollow/not filled in. The size of the zones and the sizes of the circles may correspond to typical acceptance criteria for an 18 mm image intensifier tube or a particular image intensifier tube product specification. Similar targets may be used to inspect/test other sized image intensifier tubes without departing from the invention. The zones may be used to locate a defect in an image intensifier tube and the circles may be used to measure the size of each defect. The image tube specification may limit the size and quantity of defects by zone. A defect may be a black spot, a bright spot, "chicken wire" or scintillations.

Black Spots are cosmetic blemishes in the image intensifier tube, image intensifier tube defects, or dirt or debris in the optical path of a night vision device 200. Black spots that are in the image intensifier can be inherent in the manufacturing processes or the result of damage. Black spots may be found when a predetermined amount of ambient light L1, natural or artificial, for example from a light source LS, for example a light bulb, travels through the testing device 100 and strikes the target 106A. Black spots are best viewed when most of the ambient light L1 strikes the target 106A creating a brightly lit condition.

Bright spots are defects in the image area produced by the night vision device 200. This condition may be caused by a flaw in the film on the image intensifier tube microchannel plate. A bright spot is typically a small, non-uniform, bright area that may flicker or appear constant. Bright spots are often imperceptible in environments with sufficient illumination for typical night vision device 200 operation. Bright spots are best viewed when little or none of the ambient light L1 strikes the target 106A creating a darkness condition.

Scintillations are faint, random, sparkling effect that may be found throughout the image area. Scintillation, sometimes called "video noise" despite an image intensifier tube not being a video device, is a normal characteristic of image intensifier with a microchannel plate and is more pronounced under typical night vision device 200 low-light conditions. Scintillations are best observed when a small amount of light L2, simulating starlight or moonlight, strikes the target 106A creating a high contrast condition.

Chicken wire is a hexagonal pattern of dark thin lines resembling chicken wire fencing visible in the field of view either throughout the image area or in parts of the image area. If these hexagonal patterns become overly pronounced, replacement of the image intensifier tube may be merited. Image intensifier tube specifications contain specifications for the acceptable number, size, and zone location of pronounced chicken wire artifacts. Chicken wire is best observed when a small amount of light L2, simulating starlight or moonlight, strikes the target 106A.

As noted above, the second portion 104 of the testing device 100 may be made of a diffuse light transmissive plastic, for example polytetrafluoroethylene (PTFE) thermoplastic polymer, or other material. The amount of ambient light L2 that strikes the target 106A may be varied in a variety of ways including varying the amount of light generated from the light source LS, for example with a light dimmer, by moving the testing device 100 away from the light source LS, or placing a light damper LD between the light source LS and the testing device 100.

An operator may turn the night vision device 200 "ON" and then insert the focus ring 206 in the opening 108 of the testing device 100 and rotate the night vision device 200 relative to the first portion 102 of the testing device 100 until the target 106A is in focus. The operator may locate a first defect and then determine what zone it is in by manipulating the night vision device 200 and the first portion 102 of the testing device 100 relative to the second portion 104 of the testing device 100 such that the first ring 122A, second ring 122B, and the third ring 122C are concentric with illuminated field of view of night vision device 200. The operator may then manipulate the night vision device 200 and the first portion 102 of the testing device 100 relative to the second portion 104 of the testing device 100 and the target 106A to align the first defect next to one of the series of measurement features 124. The operator may then compare the defect to the measurement features 124 to determine the defect size. The operator may then similarly determine the size of a second or subsequent defect.

Resolution is the ability of an image intensifier to distinguish between objects close together and is measured as a spacial frequency, typically using units such as line pairs per millimeter (lp/mm). Resolution is typically determined from a 1951 U.S. Air Force Resolving Power Test Target. The target is a series of different-sized patterns composed of three horizontal and three vertical lines. A user observes which of the bar patterns is the smallest that can still be distinguished as separate bars (e.g. not merged into a solid block). That smallest bar pattern is considered the resolution limit of the night vision device and is identified by the numbers next to the bar patterns (e.g. row/column numbers or group/element numbers). Because the 1951 USAF bar target requires high precision manufacturing methods to produce and may be difficult to place on a spherical surface, the 1951 USAF targets may be applied to one or more flat glass inserts which may be mechanically secured to the spherical target surface. In an alternative embodiment, an alternative test target such as a radial star, chirp, NBS 1963A or ISA/ISO may be used rather than a 1951 target.

The target 106A may also have a resolution pattern 130. The operator may turn the night vision device 200 "ON" and determine the center resolution of the image tube by manipulating the night vision device 200 and the first portion 102 of the testing device 100 relative to the second portion 104 of the testing device 100 such that the first ring 122A, second ring 122B, and the third ring 122C are concentric with illuminated field of view of night vision device 200 and then by looking through the night vision device 200 and using known resolution techniques determine the appropriate resolution. The center resolution may be determined at any light level, but typically provides the best results when the amount of light L2 striking the target 106A is low, simulating star light or moon light illumination levels.

Figure 9:
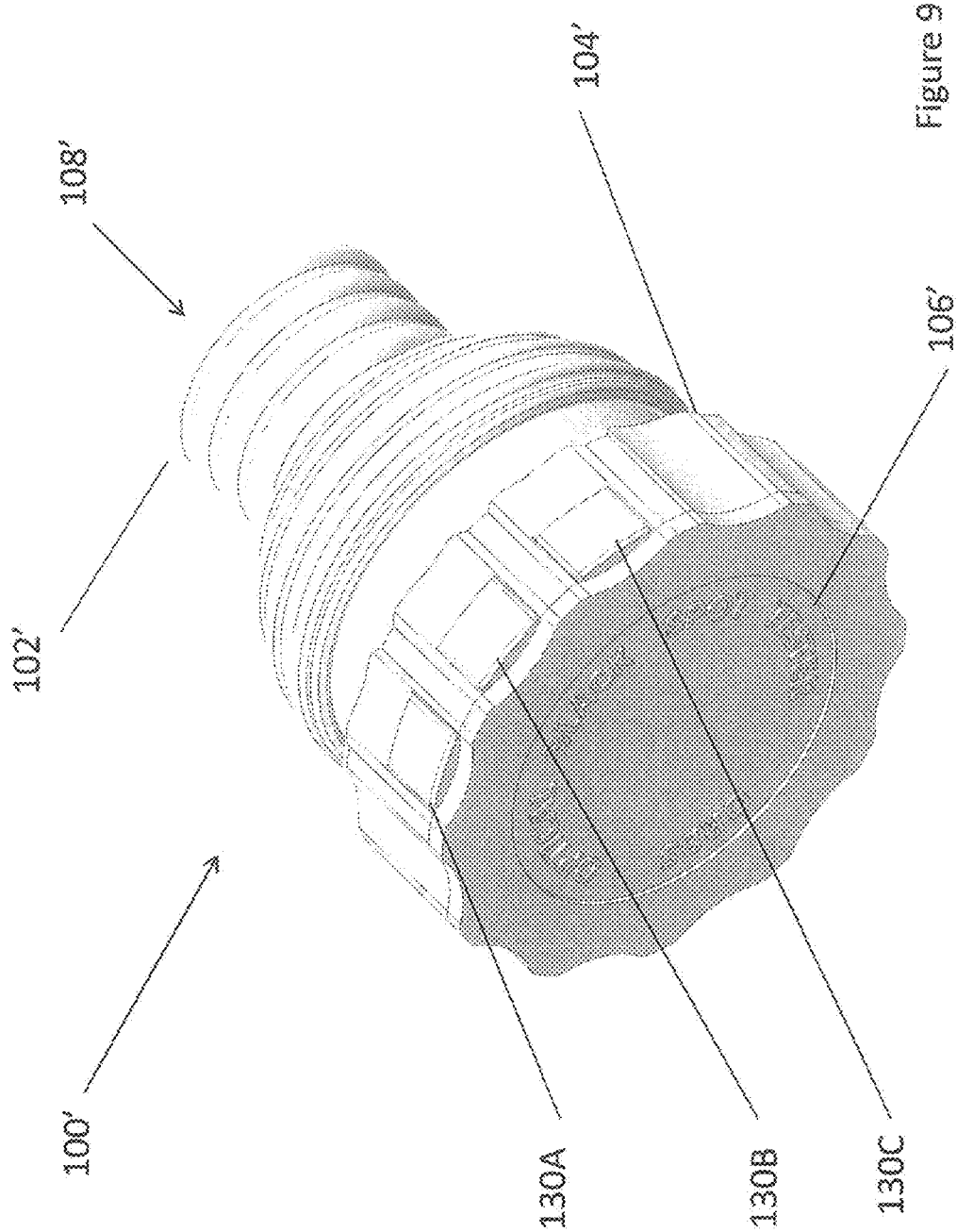
FIG. 9 is a computer rendering of a night vision testing device consistent with a second embodiment of the present disclosure.

FIG. 9 is a computer rendering of a night vision testing device 100' consistent with a second embodiment of the present disclosure; FIG. 10A is an isometric end section view of the night vision testing device 100' with a first vane 120 in a first position; FIG. 10B is an isometric end section view of the night vision testing device 100' with the first vane 120 in a second position; FIG. 10C is an isometric end section view of the night vision testing device 100' with the first vane 120 in a third position; and FIG. 11 is an end section view of the night vision testing device 100' sliced through a base portion. Testing device 100' may differ from testing device 100 in that it has the ability to control the amount of light L2 that strikes the target 106A. A plurality of actuators, for example pushbuttons 130A, 130B, and 130C, may control the opening size of a mechanical aperture. Image intensifier tubes have automatic gain adjustment; and adjusting the light level allows the image intensifier tube to be tested under very low gain, high contrast, and very high gain conditions; which correspond to a brightly lit scene, dimly lit scene (starlight or moonlight), and dark scene respectively. The lower portion 104' may diffuse the incoming light causing a more uniform illumination of the target 106A, and therefore uniform illumination of the image intensifier tube in the night vision device 200 which may improve the ability to identify defects and determine resolution.

Internal to the second portion 104' may be a first opaque vane 120 and a second opaque vane 126. The second vane 122 may be fixed to, but spaced from, the second portion 104'. The first vane 120 may be movable relative to the second portion 104' and the second vane 126. Actuation of the actuators 130A, 130B, and 130C may move the first vane from a first vane position shown in FIG. 10A to second vane position shown in FIG. 10B to a third vane position shown in FIG. 10C. In the first position, the first vane 120 blocks the least amount of the ambient light L1 passing through the second portion 104'; In the second position, the first vane 120 blocks more of the ambient light L1 passing through the second portion 104'; and in the third portion 104, the first vane 120 blocks the most ambient light L1 passing through the second portion 104'. The actuators 130A, 130B, and 130C may have a wedge, diamond, or cone shaped protrusion extending inwardly that cooperate with openings in the first vane 120 causing the first vane 120 to rotate relative to the second portion 104' and the second vane 126.

An operator may insert the focus ring 206 of the night vision device 200 in the opening 108' to begin the testing and then manipulate the actuator 130A, 130B, or 130C to adjust the amount of ambient light striking the target 106A.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

The invention claimed is:

1. A device for testing a night vision device with an image intensifier tube, comprising:
    A first housing portion having an opening to accept an objective end of a night vision device;
    A second housing portion having a target disposed along a curved surface, the second housing portion positionable relative to the first housing portion to allow an operator to align viewable defects in the image intensifier with the target.

2. The device of claim 1, wherein the target comprises a plurality of differently sized measurement features.

3. The device of claim 2, wherein the differently sized measurement dots are sized to correspond to a 0.003", 0.006", and a 0.009" defect in an image intensifier tube.

4. The device of claim 1, wherein the target comprises a United States Air Force 1951 bar resolution target.

5. The device of claim 1, wherein at least a selected one of the first housing portion and the second housing portion comprises a light transmissive diffuse material.

6. The device of claim 1, wherein the first housing portion is movable about a first axis relative to the second housing portion.

7. The device of claim 6, wherein the first housing portion is movable about a second axis relative to the second housing portion, the second axis being perpendicular to the first axis.

8. The device of claim 1, wherein the second housing portion comprises a vane to control the amount of ambient light that strikes the target.

9. The device of claim 8, wherein the vane is movable to adjust the amount of ambient light that strikes the target from a first light amount to a second light amount that is 100 times greater than the first light amount.

10. The device of claim 9, wherein the vane is movable to adjust the amount of ambient light that strikes the target from the first light amount to a second light amount that is 1000 times greater than the first light amount.

11. The device of claim 8, wherein the vane is movable through a series of predetermined positions.

12. The device of claim 8, wherein the location of the vane is moveable through a plurality of positions to adjust the amount of light striking the target.

13. The device of claim 8, wherein when the vane is in a first position, the device may be used to measure bright spots on the image intensifier tube and wherein when the vane is in a second position, the device may be used to measure dark spots on the image intensifier tube.

14. The device of claim 1, wherein the target comprises a glass insert with the United States Air Force 1951 bars for determining resolution of a night vision device.

15. The device of claim 1, wherein the opening is sized to grasp the focus ring of the night vision device to allow an operator to hold a body portion of the night vision device and rotate the second housing portion relative to the body portion of the night vision device to adjust the focus of the night vision device to see the target.

16. The device of claim 15, further comprising a neutral density filter as part of an optics in the opening.

17. The device of claim 16, wherein the optics in the opening is comprised of one or more lenses with a combined effective focal length between 50 and 300 mm.

18. The device of claim 1, wherein the first housing portion and the second housing portion rotate about a common center of rotation.

19. The device of claim 18, wherein the curved surface has a center of curvature concentric with the common center of rotation.

20. The device of claim 1, wherein the first and second housing portions are portions of concentric spheres.

* * * * *